United States Patent [19]

Mann et al.

[11] Patent Number: 5,040,535

[45] Date of Patent: * Aug. 20, 1991

[54] AVERAGE AMPLITUDE CONTROLLED RATE-RESPONSIVE PACEMAKER HAVING AUTOMATICALLY ADJUSTABLE CONTROL PARAMETERS

[75] Inventors: Brian M. Mann, Beverly Hills; John W. Poore, South Pasadena, both of Calif.

[73] Assignee: Siemens-Pacesetter, Inc., Sylmar, Calif.

[*] Notice: The portion of the term of this patent subsequent to Jul. 10, 2007 has been disclaimed.

[21] Appl. No.: 530,369

[22] Filed: May 30, 1990

Related U.S. Application Data

[63] Continuation-in-part of Ser. No. 301,935, Jan. 25, 1989, Pat. No. 4,940,053.

[51] Int. Cl.[5] .............................................. A61N 1/00
[52] U.S. Cl. ......................................... 128/419.0 PG
[58] Field of Search ........ 128/419 PG, 419 P, 419 PT

[56] References Cited

U.S. PATENT DOCUMENTS

| | | | |
|---|---|---|---|
| RE. 30,366 | 8/1980 | Rasor et al. | 128/419 P |
| 3,593,718 | 7/1971 | Krasner et al. | 128/419 P |
| 3,659,615 | 5/1972 | Enger | 128/419 P |
| 3,777,762 | 12/1973 | Nielsen | 128/419 P |
| 4,140,132 | 2/1979 | Dahl | 128/419 PG |
| 4,164,944 | 8/1979 | Alley III. et al. | 128/419 PG |
| 4,201,219 | 5/1980 | Bozal Gonzalez | 128/419 PG |
| 4,202,339 | 5/1980 | Wirtzfeld et al. | 128/419 PG |
| 4,428,378 | 1/1984 | Anderson et al. | 128/419 PG |
| 4,436,092 | 3/1984 | Cook et al. | 128/419 PG |
| 4,481,950 | 11/1984 | Duggan | 128/419 PT |
| 4,485,813 | 12/1984 | Anderson et al. | 128/675 |
| 4,513,743 | 4/1985 | van Arragon et al. | 128/419 PG |
| 4,545,380 | 10/1985 | Schroeppel | 128/419 P |
| 4,554,920 | 11/1985 | Baker Jr. et al. | 128/419 PG |
| 4,554,921 | 11/1985 | Boute et al. | 128/419 PG |
| 4,554,922 | 11/1985 | Prystowsky et al. | 128/419 PG |
| 4,556,062 | 12/1985 | Grassi et al. | 128/419 PG |
| 4,566,456 | 1/1986 | Koning et al. | 128/419 PG |
| 4,567,892 | 2/1986 | Plicchi et al. | 128/419 PG |
| 4,576,183 | 3/1986 | Plicchi et al. | 128/723 |
| 4,712,555 | 12/1987 | Thornander et al. | 128/419 PG |
| 4,719,920 | 1/1988 | Alt et al. | 128/419 PG |
| 4,722,342 | 2/1988 | Amundson | 128/419 PG |
| 4,773,401 | 9/1988 | Citak et al. | 128/419 PG |
| 4,790,318 | 12/1988 | Elmqvist et al. | 128/419 PG |
| 4,803,987 | 2/1989 | Calfee et al. | 128/419 PG |
| 4,807,629 | 2/1989 | Baudino et al. | 128/419 PG |

OTHER PUBLICATIONS

Broch, "Effects of Vibrations and Shock on Man," *Mechanical Vibration and Shock Movements*, (Brouel & Kjaer, Oct. 1980), pp. 85–96.

Servais et al., "Estimating Human Energy Expenditure Using an Accelerometer Device," (IEEE, 1982) pp. 371–374.

Wong et al., "Portable Accelerometer Device for Measuring Human Energy Expenditure," (IEEE Transactions on Biomedical Engineering, 1981), pp. 467–471.

PCT International Appl. No. PCt/DE85/00173, "Load–Related Variable Frequency Pacemaker," by Eckhard Alt.

Ionescu, "First Asian–Pacific Symposium on Cardiac Pacing," (*PACE*, May–Jun. 1980), pp. 357; 375.

*Primary Examiner*—Francis Jaworski
*Assistant Examiner*—George Manuel
*Attorney, Agent, or Firm*—Leslie S. Miller; Lisa P. Wisenberg

[57] ABSTRACT

A device for use as a rate-responsive pacemaker is disclosed in which the pacing interval is controlled by the average amplitude of a raw signal generated by a suitable physiological sensor and processed by an average amplitude converter to generate an output average amplitude signal coupled to the pacemaker control circuits to adjust the pacing interval. The average amplitude converter may be a rectifying amplifier and an integrating circuit, a voltage controlled oscillator whose frequency is measured over a suitable time interval using a time interval generator and a counter with the output of the counter being used by the control circuits of the pacemaker to vary its pacing interval, or means for measuring average amplitude of the raw signal and storing that measurement in memory and periodically processing it to alter the transfer characteristics of the rate-responsive pacemaker.

23 Claims, 3 Drawing Sheets

AVERAGE AMPLITUDE OF SENSOR SIGNAL

AVERAGE AMPLITUDE CONTROLLED RATE-RESPONSIVE PACEMAKER HAVING AUTOMATICALLY ADJUSTABLE CONTROL PARAMETERS

This application is a continuation-in-part of application Ser. No. 07/301,935, filed Jan. 25, 1989, now U.S. Pat. No. 4,940,053.

BACKGROUND OF THE INVENTION

1. Field of the Invention

The present invention relates generally to cardiac rate-responsive pacemakers, and more particularly to a cardiac rate-responsive pacemaker which responds to the average amplitude of the raw signal generated by a force transducer, such as a piezoelectric crystal or other acoustic energy transducer, used to sense physical activity associated with a user of the pacemaker.

A rate-responsive pacemaker is one wherein the basic pacing interval or rate varies as a function of some sensed parameter, such as a physiological parameter. As used herein, a broad definition of "pacing interval" or "pacing rate" is intended. This definition includes: (1) the rate at which the pacemaker provides stimulation pulses; or (2) the rate, in the case of a demand-type pacemaker, at which the pacemaker would provide stimulation pulses in the absence of naturally occurring cardiac events.

A typical rate-responsive pacemaker attempts to automatically adjust the pacing interval in order to best satisfy the physiological demands of the patient using the pacemaker. Rate-responsive pacemakers are known in the art which respond to respiration rate (see U.S. Pat. No. 3,593,718 to Krasner et al. and U.S. Pat. No. 4,567,892 to Plicchi et al.), blood temperature (see U.S. Pat. No. 4,436,090 to Cook et al.), blood oxygen saturation (see U.S. Pat. No. 4,202,339 to Wirtzfeld), or the physical activity of the patient (see U.S. Pat. No. 4,140,132 to Dahl and U.S. Pat. No. 4,428,378 to Anderson et al.).

Whatever type of physiological parameter is monitored by the rate-responsive pacemaker, some sort of sensor must be employed in order to generate an electrical signal (herein the "raw signal") which provides a measure of the selected physiological parameter. This raw signal is then used as an input signal to the circuits of the rate-responsive pacemaker in order to provide such circuits with the operating information needed to properly adjust the pacing interval.

A common problem associated with all rate responsive pacemakers relates to how the raw signal generated by the physiological sensor should be processed. That is, some sort of detection criteria must be applied in order to efficiently extract from the raw signal all proper information (e.g., true physiological activity), and exclude all improper information (e.g., noise). The prior art teaches certain signal processing techniques in order to achieve this extracting and excluding function.

For example, filtering the raw signal in order to exclude unwanted frequencies is known. Further, thresholding and frequency measurement of the signal in order to extract only those portions of the raw signal having an amplitude which exceeds a prescribed threshold level and frequency is known. Such filtering, thresholding, and frequency measurement techniques are adequate for many applications. However, for some applications these techniques of filtering, thresholding, and frequency measurement may operate to exclude relevant information and/or include irrelevant information. Accordingly, there is a need in the rate-responsive pacemaker art for improved processing circuitry for efficiently utilizing the informational content of the raw signal obtained from a physiological sensor.

Coupled with this need is the need to realize such processing circuitry inexpensively, both in terms of cost to build and power to operate, in a small space. The present invention addresses these and other objectives. Finally, the present invention must attain all of the aforesaid advantages and objectives without incurring any substantial relative disadvantage.

SUMMARY OF THE INVENTION

The disadvantages and limitations of the background art discussed above are overcome by the present invention. With this invention, the pacing interval in an implantable rate-responsive pacemaker is influenced or controlled by the average amplitude of a raw signal obtained from a physiological sensor. In a preferred embodiment, a piezoelectric crystal, or other acoustic energy transducer, is mounted in or near the implanted pacemaker and is used as a sensor of physical activity of the patient within whom the pacemaker is implanted.

Such physical activity includes body movement associated with physical activity, such as walking, running, and other normal body movements. If increased physical activity is sensed, the raw signal generated by the piezoelectric crystal or other acoustic energy transducer correspondingly increases in magnitude. If decreased physical activity is sensed, the raw signal correspondingly decreases in magnitude. The increased magnitude or decreased magnitude of the raw signal are relevant factors for accurately sensing the patient's physical activity.

In order to efficiently sense both increases and decreases in amplitude or other characteristics of the raw signal, the signal processing circuitry of the present invention looks at the average amplitude of the raw signal, rather than just at the amplitude of certain frequencies of the raw signal as has been done in the prior art. This approach allows changes in amplitude of the raw signal to have a proportional influence to the need to change the pacing interval. As such, this approach functions whether or not the amplitude is above or below some arbitrary threshold level, and whether or not the frequency is within some prescribed frequency spectrum.

The processing circuitry used to determine the average amplitude of the raw signal in accordance with the present invention includes an acoustic energy transducer, such as a piezoelectric crystal or equivalent sensor which generates a raw signal in response to physical force applied thereto, an amplifier to amplify the raw signal generated by the acoustic energy transducer, and means for determining the average amplitude of the amplified raw signal.

In one embodiment, this means for determining the average amplitude of the raw signal includes processing means for processing the raw signal in a prescribed manner, a voltage controlled oscillator (VCO), and a frequency counter. The processing means further amplifies the amplified raw signal, but does so in a non-linear fashion, and the output of the processing means drives a suitable VCO. The VCO generates a fixed amplitude signal whose frequency is substantially proportional to the average amplitude of the processed amplified signal applied thereto.

The VCO frequency is measured and averaged over a suitable prescribed interval of time by the frequency counter. At the end of the measuring time interval, the content of the frequency counter thus provides a digital signal which may be applied directly to the control logic circuits of the pacemaker in order to appropriately control the pacing interval.

Alternatively, at the end of the measuring time interval, the contents of the frequency counter may be stored in a memory and further processed over time with other frequency counter values similarly stored in order to appropriately alter the operating characteristics of the pacemaker. Another alternative is to process the non-linearly amplified raw signal using a conventional analog control circuit to relate acoustic energy to pacing rate by a control function which the control circuit implements.

DESCRIPTION OF THE DRAWINGS

These and other advantages of the present invention are best understood with reference to the drawings, in which.

DETAILED DESCRIPTION OF THE PREFERRED EMBODIMENT

Figure 1:
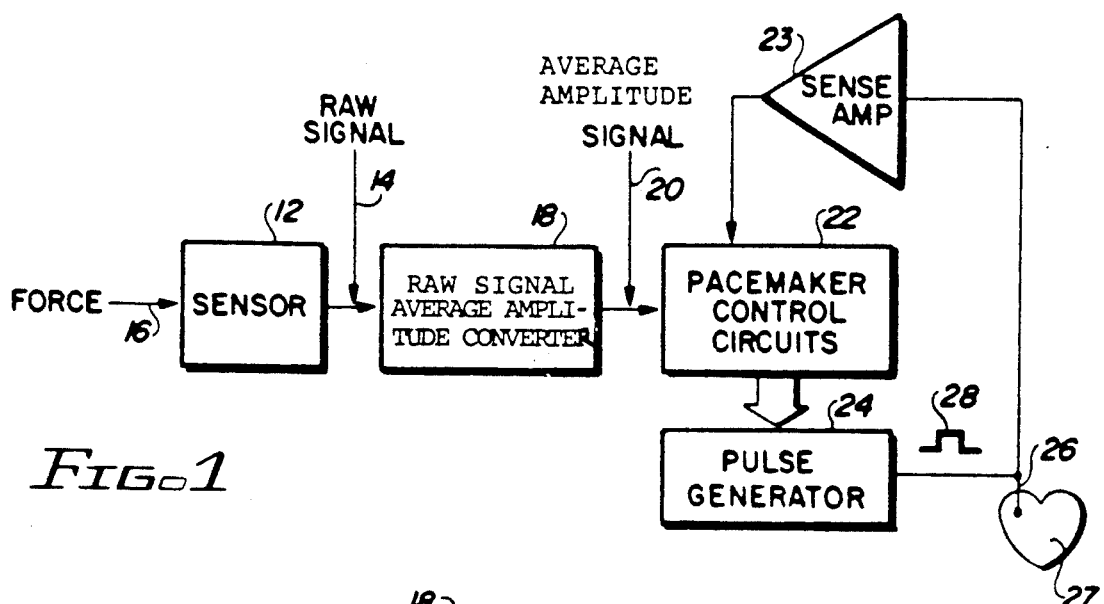
FIG. 1 is a block diagram of the circuits used to process a raw signal in accordance with the teachings of the present invention.

The present invention is shown in FIG. 1, which illustrates a rate-responsive pacemaker which includes a suitable sensor 12 which generates a raw signal 14 in response to a physical or other force 16. The raw signal 14 is applied to a raw signal average amplitude converter 18 from which an average amplitude signal 20 is generated. The average amplitude signal 20 is applied to the control circuits 22 of the pacemaker, and these control circuits 22 are coupled to a pulse generator 24.

The pulse generator 24 generates a stimulating pulse 28 at appropriate times as controlled by the control circuits 22. The stimulating pulse 28 is applied to a heart 27 over a suitable conductor 26, such as a pacing lead. In a demand pacemaker, this same conductor 26 which carries stimulating pulses 28 to the heart 27 also is connected to a sense amplifier 23. The sense amplifier 23 is configured to sense natural cardiac activity, such as, for example, P-waves or R-waves, and to inhibit the delivery of the stimulus pulse if any such natural activity is sensed.

The pacemaker control circuits 22 and the pulse generator 24 of the rate-responsive pacemaker of the present invention may be the same types of circuits which are employed in other rate-responsive pacemakers, for example, those circuits described in the previously cited U.S. patents. Reference is also made to U.S. Pat. No. 4,712,555, which patent describes the operation of one type of rate-responsive pacemaker, and which patent is hereby incorporated herein by reference. These patents contain the necessary teachings for enabling one skilled in the art to develop and use the control circuits and pulse generator circuits of a rate responsive pacemaker.

Accordingly, no detailed description of the control circuits 22 or the pulse generator 24 will be presented herein. Suffice it to state that the control circuits 22 typically include the ability to operate the pacemaker in a demand-type mode of operation wherein the pulse generator 24 generates a stimulating pulse 28 only in the absence of spontaneous cardiac activity. Further, such a rate-responsive pacemaker will typically also include means for noninvasively programming various control parameters associated with operation of the pacemaker through a suitable communication link, not shown, in order to allow the pacemaker to be used in a wide variety of applications and with a wide variety of patients.

Figure 2:
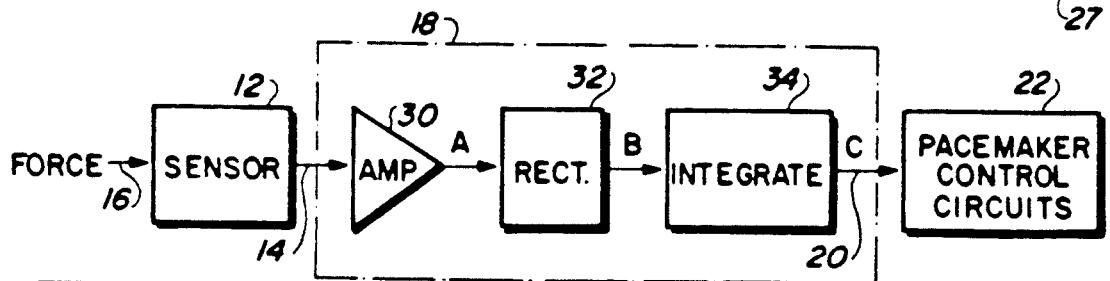
FIG. 2 is a block diagram showing one embodiment of the raw signal average amplitude converter of FIG. 1.

The present invention is directed primarily to the raw signal average amplitude converter 18 and the method which is used to convert the raw signal 14 to an appropriate average amplitude signal 20. One embodiment of the raw signal average amplitude converter 18 is illustrated in the block diagram of FIG. 2. In FIG. 2, it may be seen that the raw signal 14 is applied to an amplifier 30. The output of the amplifier 30 is then rectified by a rectifier 32, and the rectified signal is then integrated by an integrating circuit 34. The amplifier 30 and the rectifier 32 comprise the non-linear amplifier referred to herein.

Figure 3:
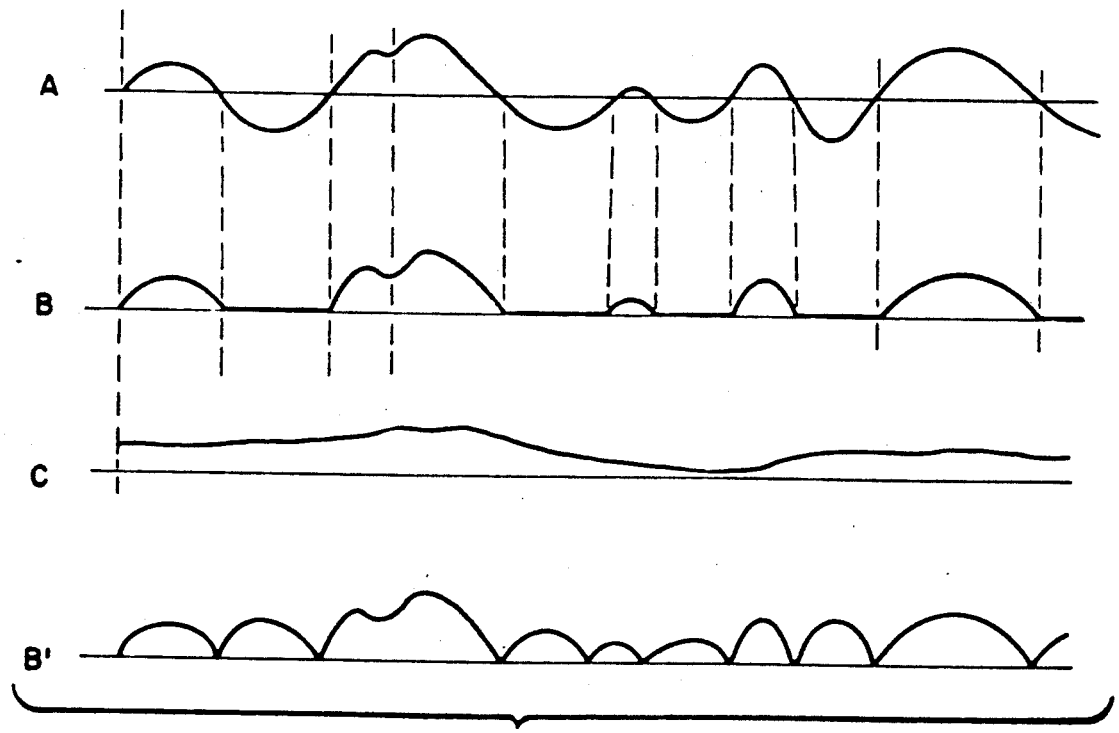
FIG. 3 is a waveform diagram illustrating some of the waveforms associated with the operation of the circuit of FIG. 2.

In FIG. 3, some of the signals associated with the operation of the raw signal average amplitude converter 18 of FIG. 2 are shown. The output of the amplifier 30 in FIG. 2 is designated by the nomenclature "A." The output of the rectifier circuit 32, which is the preferred embodiment in a half wave rectifier, is designated by the nomenclature "B." The negative portion of the signal may be used instead of the positive portion of the signal shown in FIG. 3. Indeed, in circumstances in which there are high positive peaks in the signal, it may be preferable to use the negative portion of the signal. Alternately, a full wave rectifier could be used to produce the output designated by the nomenclature "B'." Similarly, the output of the integrating circuit 34 is designated by the nomenclature "C."

As seen in FIG. 3, the amplifier 30 output signal "A" is a signal which varies as a function of the force 16 which is applied to or otherwise sensed by the sensor 12. The rectifying circuit 32 half wave rectifies the signal "A" in order to produce the signal "B." The rectified signal "B" is then integrated by integrating circuit 34 in order to produce the signal "C." Because the signal "C" is the integrated amplitude of the half wave rectified "B" signal, its value increases or decreases as the area under the curve of waveform "B" increases or decreases.

The signal "C" is then applied to the pacemaker control circuits 22 in order to provide a control signal which may be used to indicate that the pacing interval of the pacemaker needs to be changed. As illustrated in FIG. 3, the control signal "C" (which is also identified in the figures as the average amplitude signal 20) is an analog signal. The pacemaker control circuits 22 may be designed to receive and respond to such an analog signal. However, typically the average amplitude signal 20 will be converted to a digital signal.

Thus, the pacemaker control circuits 22 may include an analog-to-digital (A-to-D) converter (not shown), which is well known in the art. Alternatively, the signal may be digitized as explained below in connection with FIG. 4. Integration in a digital system may take place within the digital system instead of within the integrator 34 shown.

Figure 4:
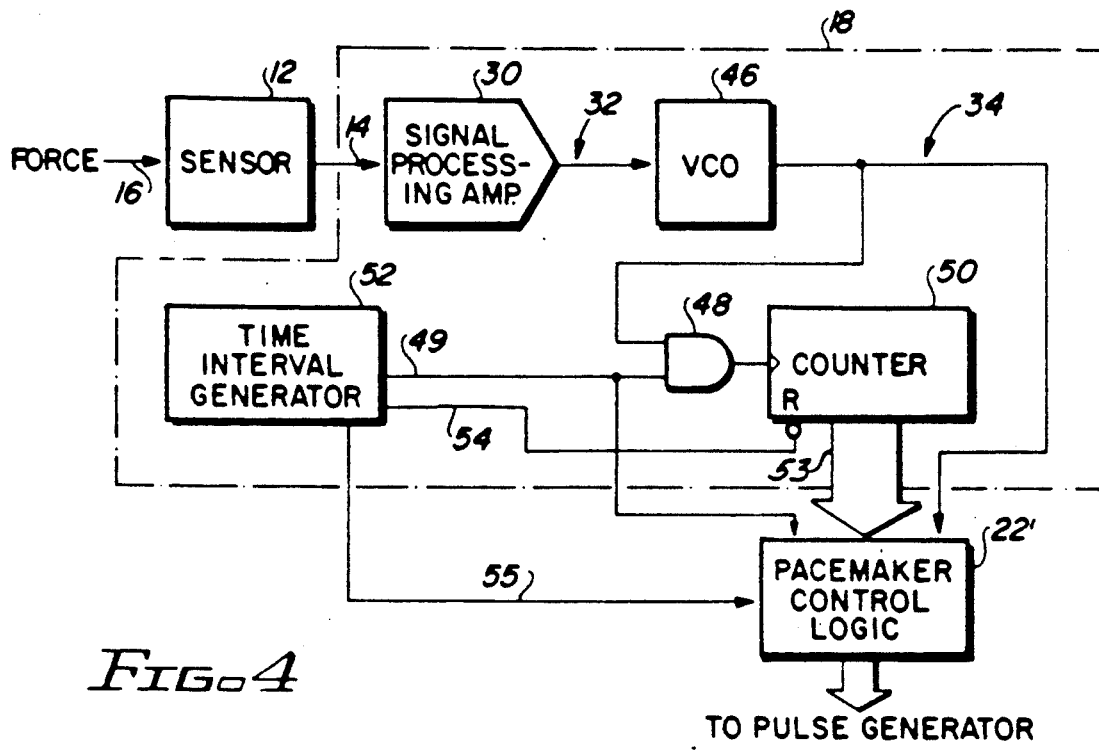
FIG. 4 is a block diagram showing another embodiment of the raw signal average amplitude converter of FIG. 1.

Referring now to FIG. 4, another embodiment of the raw signal average amplitude converter 18 is illustrated in block diagram form. In accordance with this embodiment, the raw signal 14 is applied to a signal processing amplifier 30. This processing amplifier 30 may be a non-linear amplifier, a threshold detector, a comparator circuit, a rectifying circuit, or a combination of such circuits. It should be noted, for example, that a halfwave rectifying amplifier circuit may be viewed as a threshold detector, with approximately a zero-volt threshold, as well as a non-linear amplifier, amplifying signals of only one polarity and attenuating or blocking signals of the other polarity.

In one embodiment, the amplifier 30 comprises a half wave rectifying amplifier, and the output signal 32 obtained therefrom is similar to that shown as waveform B in FIG. 3.

The output signal 32 from the processing amplifier 30 is applied to a voltage controlled oscillator (VCO) 46. The output signal 34 from the VCO 46 is thus a variable frequency signal having a frequency which varies (or varies inversely) as a function of the amplitude of the output signal 32 from the processing amplifier 30. For the embodiment where the output from the amplifier 30 is substantially as shown in waveform B of FIG. 3 —that is, where processing amplifier 30 comprises a half wave rectifying amplifier—the frequency of the VCO signal 34 will vary greatly as indicated in the waveform diagram of FIG. 5.

The output signal 34 from the VCO 46 is applied through a functional AND gate 48 to a digital counter circuit 50. Each cycle of the VCO 46 is counted in the digital counter 50 during a time interval defined by a time interval generator 52. This time interval is defined by a gating signal which appears on a signal line 49. As shown in FIG. 4, the signal on the line 49 from the time interval generator 52 is also connected to the gate 48. Hence, only when the time interval gating signal 49 enables the gate 48 can the output of the VCO 46 be counted in the counter 50.

Figure 5:
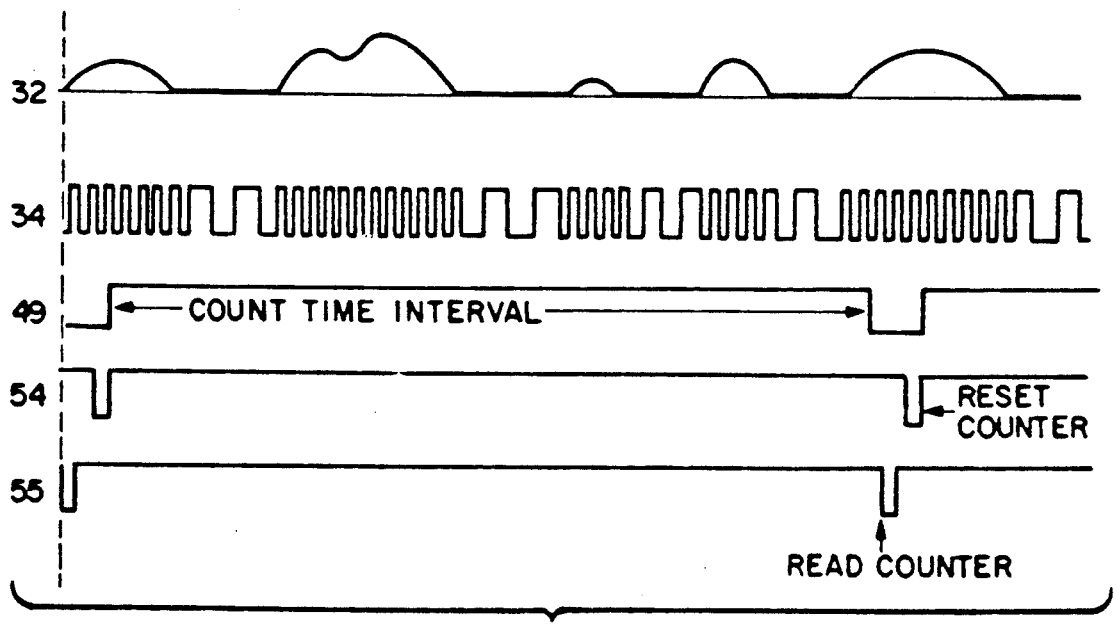
FIG. 5 is a waveform diagram illustrating some of the waveforms associated with the operation of the circuit of FIG. 4.

Representative signal waveforms associated with operation of the circuit of FIG. 4 are included in FIG. 5, where the signals are identified by the reference numeral of the signal line on which they appear. It may be noted that the time interval gating signal 49 is identified as the COUNT TIME INTERVAL in FIG. 5.

The counter 50, as is known in the art, may be realized by a plurality of flip-flops connected in series. At the conclusion of the COUNT TIME INTERVAL, the time interval generator 52 generates a read signal 55 which allows the count held in the counter 50 to be transferred to the pacemaker control logic 22 over the read bus 53. Once this count has been read, the counter 50 is reset with a reset signal sent over the signal line 54, thereby preparing the counter 50 to measure the VCO frequency during the next COUNT TIME INTERVAL.

The count held in the counter 50 at the end of the COUNT TIME INTERVAL is a digital word signal which represents an integrated measure of the VCO frequency over that time interval. This digital word signal or value may be passed directly over the data bus 53 to the pacemaker control logic circuits 22' of the rate-responsive pacemaker, which circuits 22' are also digital circuits. Thus, the need for a separate Analog-to-Digital converter circuit is obviated, and the circuitry is kept simple and inexpensive, yet effective.

Because the VCO 46 generates a signal having a frequency proportional to the voltage amplitude of the signal 32 applied thereto, and because the voltage amplitude applied thereto is related to the average amplitude of the raw signal 14, the count held in the counter 50 is also related to the average amplitude of the raw signal. As indicated above, this count is already advantageously converted to a digital signal which may be used directly by the pacemaker control logic 22'. Thus, the pacemaker control logic 22' controls the pacing rate as a function of the average amplitude of the raw signal.

Such control may be readily accomplished by those skilled in the art either algorithmically or by table lookup. That is, within the control logic 22', or within circuits coupled thereto, a suitable algorithm may be programmed which calculates the pacing rate as a function of the digital signal obtained from the counter 50. Alternatively, a table stored within the memory circuits of the pacemaker may define the pacing rate as a function of the digital signal obtained from the counter 50.

Figure 6:
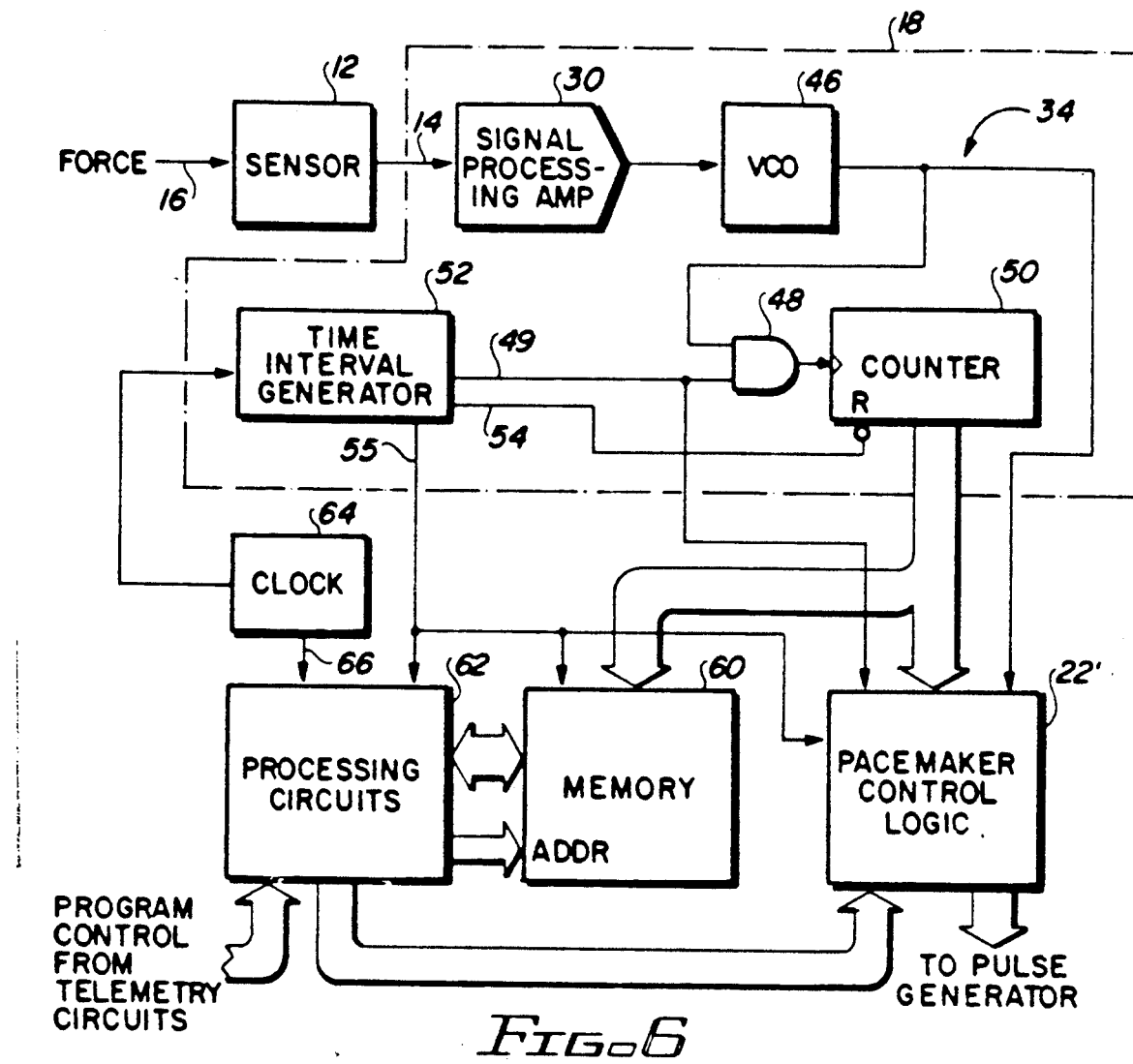
FIG. 6 is a block diagram of another embodiment of the invention wherein memory and processing circuitry is included to condition or alter the rate-responsive control circuits of the pacemaker as a function of prior activity which has been sensed.

Referring next to FIG. 6, the pacemaker control logic 22' may also include, or be interfaced with, appropriate memory elements 60 wherein the count held in the counter 50 is stored and saved for subsequent retrieval and analysis. By storing the count values over a prescribed period of time, which could be several hours, days, weeks, or even months, the pacemaker control logic 22', in conjunction with suitable processing circuitry 62, is able to monitor and process these stored count values (which count values represent the average amplitude of the sensor's raw signal) in order to optimally control the operation of the pacemaker.

For example, the processing circuitry 62 may include, or be controlled by, an appropriate algorithm that automatically adjusts at least one of the rate responsive pacemaker control parameters, such as the minimum rate $R_{min}$ (see FIG. 7), as a function of the average amplitude signals sensed over a prescribed period of time. This prescribed period of time, which could be selectable through a pacemaker programming operation, could be the past two or three days, or even the past two or three weeks, which period of time could be measured by monitoring an appropriate clock signal 66 from the clock circuit 64.

In this way, the pacemaker rate-responsive control circuits become "conditioned" to respond to long-term changes which occur in the patient's activity, which activity is sensed through the sensor 12. This conditioning of the pacemaker control circuits may produce an effect similar to the natural conditioning which occurs in a healthy person as a result of a long-term change in physical activity, such as a long-term, consistent exercise program.

An example of how the processing circuitry 62 of FIG. 6 could alter or condition the operation of the rate responsive pacemaker over a period of time as a function of the activity or average amplitude signals which are sensed over such period of time will be presented next. Before presenting such an example, however, reference is first made to FIG. 7 where the transfer characteristics of a typical rate responsive pacemaker are shown. The vertical axis of FIG. 7 represents the pacing rate, identified as R, while the horizontal axis represents the average amplitude of the raw signal from the sensor 12, identified as X.

Figure 7:
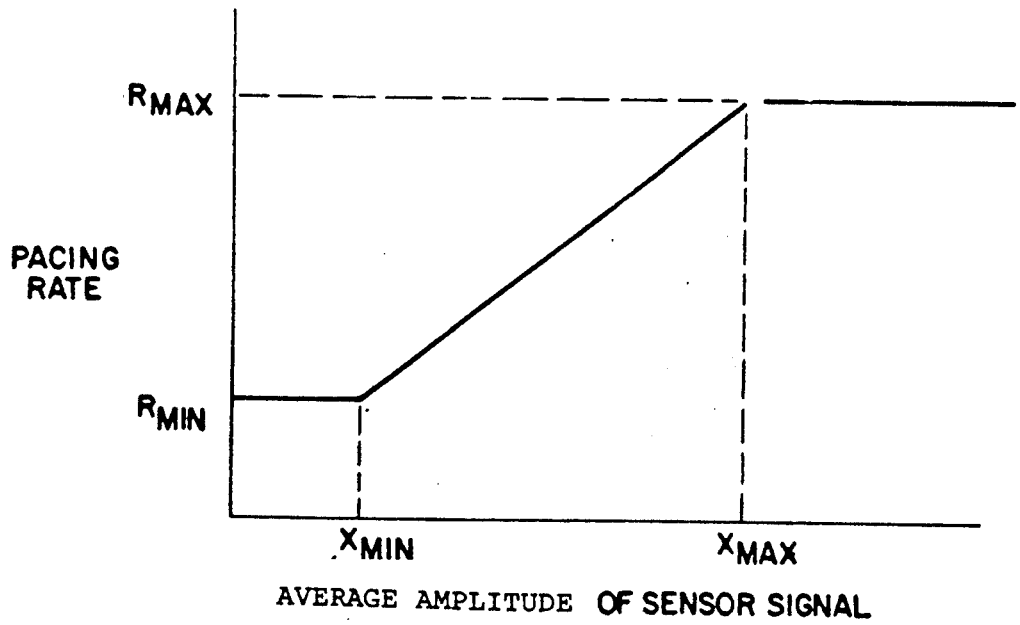
FIG. 7 shows a representative transfer curve of a rate-responsive pacemaker.

As indicated in FIG. 7, there are four points on the transfer curve which significantly influence the operation of the pacemaker. These points include the minimum pacing rate, $R_{min}$, and the maximum pacing rate, $R_{max}$. The pacemaker, as controlled by the pacemaker control logic 22' and/or processor 62, operates at the minimum pacing rate, $R_{min}$, so long as the average amplitude of the sensor signal remains below a minimum value, $X_{min}$. Similarly, the pacemaker operates at the maximum pacing rate, $R_{max}$, so long the average amplitude of the sensor signal remains above a maximum value, $X_{max}$.

If, however, the average amplitude of the sensor signal lies between $X_{min}$ and $X_{max}$, the pacing rate will vary as a function of the average amplitude of the raw signal according to a prescribed relationship. This prescribed relationship is depicted in FIG. 7 as a linear relationship. It should be noted, however, that any desired relationship, not just a linear relationship, could be used to relate the average amplitude of the raw signal from the sensor 12 to the pacing rate between the $R_{min}$ and $R_{max}$ points.

Still referring to FIG. 7, it may be noted that this transfer operation of transferring or converting the sensed average amplitude from the physiological signal (for example, the raw signal 14 from the sensor 12) to a pacing rate may be achieved by those skilled in the art in a variety of ways. For example, the transfer operation may be achieved within the processing circuits 62 and/or control logic 22' either algorithmically or by table look-up, as described above.

With reference to FIG. 6 and FIG. 7, an example will now be given of how the operation of the rate responsive pacemaker could be "conditioned" based on the average amplitude of the raw signal 14 over a prescribed period of time. At a particular sample time the average amplitude of the raw signal 14 is determined using a suitable raw signal average amplitude converter 18. The resulting average amplitude signal, representative of the average amplitude of the raw signal at the particular sample time, is stored in the memory 60 at a known address as determined by the processing circuit 62. For example, the average amplitude signal could be time-logged into the memory 60 in a way that identifies the time at which the average amplitude sample was taken.

Alternatively or conjunctively, an average, mean or other representative average amplitude signal over a prescribed period of time may be calculated by the processing circuits 62 and stored in the memory 60 at a known address. The average amplitude signals stored over a relatively long period of time, such as over the past one or two week period, are then periodically (e.g., once a day) examined by the processor 62. If such examination identifies a significant long-term trend, i.e., an increase or decrease in the average amplitude of the raw signal, then appropriate changes are automatically made, as defined algorithmically or through table look-up, to one or more of the controlling parameters (for example, $X_{min}$ and/or $X_{max}$ as defined in FIG. 7) of the rate-responsive pacemaker.

In order to provide added flexibility and versatility in how the rate-responsive pacemaker responds for each unique patient, means are provided whereby the algorithm or table look-up technique (used to define which and how the controlling parameters are affected by a long-term trend identification) may be programmably altered by an attending physician or other medical personnel. Such programming changes may be accomplished by techniques known in the art using the pacemaker's telemetry channel circuits and an external programming device.

As described in the example above, the long-term trends which are identified by the processing circuitry 62 (which trends are used to automatically adjust one or more controlling parameters of the pacemaker) are limited to trends associated with the sensor's raw signal as stored in memory 60. It is to be understood, however, that other types of long-term trends could also be identified and used for this purpose.

For example, with the availability of modern low power memory circuits, the memory 60 could be large enough to store a great deal of data associated with the operation of the pacemaker as well as the heart's natural activity as sensed by the pacemaker. Such data could be processed, either prior to or after storing it in the memory 60, for the purpose of identifying other types of trends, such as a long term change in the at-rest or active natural heart rate, the ratio of stimulated heart beats to natural heart beats, etc. Such trends, if identified, could also be used to alter one or more controlling parameters of the rate responsive pacemaker as described above. Long term trends could also be due to changes in the sensor or in its environment. Such long term trends could be compensated for in similar fashion.

In the preferred embodiment, the sensor 12 is an activity sensor adapted to sense the physical activity of the patient using the pacemaker. However, it is to be understood that the principles of the present invention apply to processing the raw signal from any type of physiological sensor which may be employed. In the preferred embodiment, the sensor 12 is realized with a piezoelectric crystal or other acoustic energy transducer. As known in the art, a piezoelectric crystal or other acoustic energy transducer responds to a physical force 16 applied thereto by generating an electrical signal.

The electrical signal generated in response to the application of force is the raw signal 14. Typically the sensor 12—that is the piezoelectric crystal or other acoustic energy transducer—is placed within the case of the pacemaker. Hence, any forces applied to the pacemaker, such as would occur by the patient's breathing, walking, rising from a sitting to a standing position, rolling from one position to another while lying down, and the like, would be evidenced in the raw signal. If the raw signal 14 indicates that the sensed physical activity has either increased or decreased for a sufficient period of time (which period of time could be defined by either the time interval generator 52, the pacemaker control logic 22', the processing circuits 62, or combinations thereof) then appropriate action is taken in order to increase or decrease the pacing interval.

In one embodiment, as described above in conjunction with the description of FIGS. 4 and 5, the time interval generator 52 measures (counts) the number of cycles in the output signal 34 of the VCO, and thereby averages the average amplitude of the raw signal, for a prescribed time interval, indicated in FIG. 5 as the COUNT TIME INTERVAL. In a programmable-type pacemaker, this time interval is a programmed parameter. Typically, the time interval is on the order of between 5 and 45 seconds, thereby assuring that only a sustained physical activity, as sensed by the sensor 12, operates to allow the pacing interval to be modified.

In contrast to the rather narrow band amplifiers which are taught in the prior art, the signal processing amplifier 30 (FIG. 4 and FIG. 6) has a fairly wide frequency band associated therewith. Typically, the frequency response of the amplifier 30 will be from 0.1 Hz. to around 100 Hz. Further, when the amplifier 30 performs a rectifying function, the circuit is kept simple by amplifying only negative excursions of the raw signal, not positive excursions (or vice versa).

The VCO 46, the time interval generator 52, and the counter 50 may be realized with suitable circuits known in the art. Similarly, with reference to FIG. 6, the processing circuits 62 may be realized using a suitable microprocessor circuit, and the memory 60 may be realized using commercially available memory circuits, such as a 256K×8 bit RAM memory chip. The response of the VCO 46 need not be linear, although, preferably, it should be repeatable, thereby allowing the pacemaker control logic 22' to respond appropriately to whatever changes are sensed in the count held in the counter 50.

All of the circuits within the raw signal average amplitude converter 18, and all of the digital circuits within the pacemaker, are preferably realized using CMOS integrated circuits, which circuits consume little power in comparison with other types of integrated circuits. Moreover, preferably all of the circuits within the raw signal average amplitude converter 18 may be fabricated on a single semiconductor chip as part of a single integrated circuit, thereby significantly reducing the overall size of the circuits. In practice, such circuitry may be included on the same chip(s) as are the pacemaker control circuits 22, the pacemaker control logic 22', the processor circuits 62, or the memory circuits 60.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A rate-responsive pacemaker comprising:
    pulse generating means for generating stimulating pulses;
    control means for controlling the rate at which said pulse generating means generates said stimulating pulses;
    sensor means for sensing a physiological parameter and for generating an electrical signal representative of said sensed physiological parameter; and
    signal processing means for processing said electrical signal and for generating a control signal representative of the average amplitude of said electrical signal, said control signal being applied to said control means, and said control means being responsive at least in part to said control signal in controlling the rate at which said stimulating pulses are generated, wherein said signal processing means comprises:
    rectifying amplifier means for amplifying and rectifying said electrical signal;
    voltage controlled oscillator means coupled to the output of said rectifying amplifier means for generating an oscillator signal having a frequency that varies as a function of the signal output from said rectifying amplifier means; and
    measurement means for measuring the frequency of said oscillator signal over a prescribed time interval, said frequency measurement comprising said control signal.

2. The rate-responsive pacemaker of claim 1, wherein said measurement means comprises:
    a counter circuit that counts the signal excursions of a prescribed type (e.g., positive or negative) occurring in the oscillator signal over said prescribed time interval, and that holds said count at the conclusion of said prescribed time interval, said count held in said counter circuit comprising a digital representation of said control signal.

3. The rate-responsive pacemaker of claim 2, wherein said signal processing means further comprises:
    filtering means for filtering said electrical signal generated by said sensor means prior to applying said electrical signal to said rectifying amplifier means.

4. A rate-responsive pacemaker comprising:
    pulse generating means for generating stimulating pulses;
    control means for controlling the rate at which said pulse generating means generates said stimulating pulses;
    sensor means for sensing a physiological parameter and for generating an electrical signal representative of said sensed physiological parameter; and
    signal processing means for processing said electrical signal and for generating a control signal representative of the average amplitude of said electrical signal, said control signal being applied to said control means, and said control means being responsive at least in part to said control signal in controlling the rate at which said stimulating pulses are generated, wherein said signal processing means comprises:
    rectifier means for rectifying said electrical signal generated by said sensor means; and
    integrating means for integrating the rectified signal obtained from said rectifier means and for generating an output signal representative of the integration of said rectified signal, said output signal comprising the control signal that is applied to said control means.

5. The rate-responsive pacemaker of claim 4, wherein said signal processing means further comprises:
    filtering means for filtering said electrical signal generated by said sensor means prior to applying said electrical signal to said rectifier means.

6. The rate-responsive pacemaker of claim 4, wherein said signal processing means further comprises:
    amplifier means for amplifying said electrical signal generated by said sensor means prior to applying said electrical signal to said rectifier means.

7. In a rate-responsive pacemaker adapted to provide stimulating pulses to a heart at a controlled rate, which controlled rate includes the ability to vary an escape interval when said pacemaker is operating in a demand mode of operation, and which controlled rate is controlled at least in part by a control signal, a signal processing system for generating said control signal as a function of a raw signal outputted from a physiological sensor, said raw signal having an average amplitude indicative of a physiological parameter sensed by said physiological sensor, said signal processing system comprising:

amplifier means for amplifying said raw signal and for producing an amplified raw signal, said amplified raw signal having an average amplitude associated therewith proportional to the average amplitude of said raw signal; and control signal generating means responsive to said amplified raw signal for generating said control signal as a function of the average amplitude of said amplified raw signal.

8. The pacemaker signal processing system of claim 7, wherein said control signal generating means comprises:

rectifying means for rectifying the amplified raw signal in a prescribed manner and for producing a rectified output signal, said rectified output signal having an average amplitude proportional to the average amplitude of said raw signal;

variable frequency oscillator means responsive to said rectified output signal for generating a processed signal having a frequency that varies as a function of the average amplitude of the signal rectified by said rectifier means; and measurement means for measuring the frequency of said processed signal generated by said variable frequency oscillator means, a frequency measurement obtained from said measurement means comprising a base signal from which said control signal is derived.

9. The pacemaker signal processing system of claim 7, wherein said physiological sensor comprises:

a force sensor for sensing acoustic energy.

10. The pacemaker signal processing system of claim 9, wherein said force sensor comprises:

a piezoelectric crystal.

11. The pacemaker signal processing system of claim 7, wherein said control signal generating means comprises:

rectifier means for rectifying the amplified raw signal and for producing a rectified output signal having an average amplitude proportional to the average amplitude of said raw signal; and averaging means for averaging the average amplitude of the rectified output signal, the resulting average output signal of said averaging means comprising a base signal from which said control signal is derived.

12. A method of processing a raw signal obtained from a physiological sensor used with a rate-responsive pacemaker to produce a control signal, said control signal being used by said pacemaker to control the pacing interval thereof, said method comprising the steps of:

(a) determining the amount of average amplitude of said raw signal; and (b) generating said control signal as a function of the average amplitude determined in step (a).

13. The method of claim 12 wherein step (a) comprises:

(1) rectifying the raw signal;

(2) applying the resulting rectified signal to a voltage controlled oscillator; and (3) counting the number of cycles in the output signal of said voltage controlled oscillator over a prescribed time interval, said counted cycles comprising an indication of the average amplitude of the raw signal.

14. In a rate-responsive pacemaker adapted to provide stimulating pulses to a heart at a controlled rate on demand as a function of sensed physiological need, and wherein the controlled rate is determined by a prescribed transfer function that relates the sensed physiological need to the pacing rate, an adaptive system for automatically altering the prescribed transfer function comprising:

means for sensing a physiological need of a user of said rate-responsive pacemaker at prescribed intervals, and for generating a physiological signal indicative of such need during said prescibed intervals, each physiological signal thus generated having an average amplitude associated therewith;

pulse generating means for producing stimulating pulses on demand at a rate controlled by a rate control signal;

control means for generating said rate control signal during a given interval as a function of the average amplitude of the physiological signal corresponding to said given interval, the relationship between said rate control signal and the average amplitude of said physiological signal comprising said prescribed transfer function, said prescribed transfer function being alterable as a function of at least one transfer-function control parameter;

memory means for selectively storing said physiological signals;

trend processing means for identifying trends in the physiological signals stored in said memory means over a plurality of said prescribed intervals; and means for altering said at least one transfer-function control parameter as a function of the trends identified by said trend processing means;

whereby the prescribed transfer function of said rate-responsive pacemaker is automatically altered as a function of identified trends in the physiological needs of said user.

15. The adaptive system for altering the prescribed transfer function of a rate-responsive pacemaker of claim 14, wherein said physiological sensing means comprises:

means for sensing natural and stimulated cardiac activity of said user.

16. The adaptive system of claim 14, wherein said physiological sensing means comprises:

means for sensing physical activity of said user.

17. The adaptive system of claim 16, wherein said physical activity sensing means comprises:

an acoustic energy transducer that produces an electrical output signal in response to acoustic energy applied thereto, and wherein the physiological signal generated by said physiological sensing means is generated as a function of the average amplitude of said electrical output signal.

18. A rate-responsive pacemaker comprising:

stimulating means for selectively generating stimulating pulses on demand in response to a control signal;

first sensing means for sensing natural cardiac activity;

second sensing means for sensing physiological need, said second sensing means comprising:
  transducer means for converting physical forces applied thereto to an electrical output signal, and
  signal processing means for determining the average amplitude of said electrical output signal and for generating an average amplitude signal representative of said average amplitude; and
control means responsive to said first and second sensing means for generating said control signal as a function of sensed cardiac activity and said average amplitude signal in accordance with a prescribed transfer function, and for identifying trends in cardiac activity and physiological need sensed over a prescribed time period, and for altering said prescribed transfer function in response to the identification of said trends.

19. The rate-responsive pacemaker of claim 18, wherein said signal processing means comprises:
  rectifying means for rectifying the electrical output signal from said transducer means;
  voltage controlled oscillator means for generating a VCO output signal having an instantaneous frequency that varies as a function of the rectified signal obtained from said rectifying means; and
  counting means for counting the number of cycles present in said VCO output signal over a prescribed time interval, said counting means including a counter, the count held in said counter at the conclusion of said time interval providing a digital representation of the average amplitude of the electrical output signal of said transducer means over said prescribed period of time.

20. A rate-responsive pacemaker comprising:
  stimulating means for selectively generating stimulating pulses on demand in response to a control signal;
  sensing means for sensing physiological need, said sensing means including means for generating a raw signal having an average amplitude indicative of physiological need; and
  control means responsive to said sensing means for generating said control signal as a function of a prescribed transfer function between said control signal and the average amplitude of said raw signal, said control means including:
    trend identification means for identifying trends in physiological need sensed over a prescribed time period, and
    control signal altering means for altering the prescribed transfer function in response to the identification of said trends by said trend identification means.

21. A rate-responsive pacemaker including means for generating stimulating pulses on demand as a function of sensed physiological need, the improvement comprising:
  sensor means for generating a raw signal, said raw signal having an average amplitude that varies as a function of at least one physiological parameter; and
  processing means for determining the average amplitude of said raw signal, said average amplitude being used thereafter by said rate-responsive pacemaker as an indicator of physiological need.

22. The rate-responsive pacemaker of claim 21 further comprising:
  memory means for storing the average amplitude of said raw signal over a prescribed period of time; and
  processing means for identifying trends in the average amplitude of the raw signal stored in said memory means, said trend identification being used by said pacemaker to alter the manner in which said stimulating pulse generating means generates the stimulating pulses.

23. The rate-responsive pacemaker of claim 18, wherein said second sensing means comprises:
  transducer means for converting physical forces applied thereto to an electrical output signal; and
  signal processing means for determining the average amplitude of said electrical output signal and for generating an average amplitude signal representative of said average amplitude, said average amplitude signal being utilized by said control means to control, at least in part, the generation of said control signal.

* * * * *